(12) United States Patent
Warner

(10) Patent No.: US 8,062,482 B2
(45) Date of Patent: Nov. 22, 2011

(54) ACETALDEHYDE REMOVAL FROM METHYL ACETATE BY DISTILLATION AT ELEVATED PRESSURE

(75) Inventor: R. Jay Warner, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 857 days.

(21) Appl. No.: 11/978,882

(22) Filed: Oct. 30, 2007

(65) Prior Publication Data
US 2009/0107833 A1 Apr. 30, 2009

(51) Int. Cl.
*B01D 3/42* (2006.01)
*C07C 47/09* (2006.01)
*C07C 51/44* (2006.01)
*C07C 67/54* (2006.01)

(52) U.S. Cl. ......... 203/1; 203/2; 203/3; 203/29; 203/91; 203/DIG. 21; 203/DIG. 23; 560/231; 560/248; 562/519; 562/608; 568/420; 568/487; 568/492

(58) Field of Classification Search ................ 203/1–3, 203/14–18, 29, 91, 98, DIG. 21, DIG. 23; 560/231, 248; 562/519, 608; 568/420, 487, 568/492
See application file for complete search history.

(56) References Cited

U.S. PATENT DOCUMENTS

| | | | | | |
|---|---|---|---|---|---|
| 4,361,707 | A | * | 11/1982 | Habib et al. | 568/487 |
| 5,625,095 | A | * | 4/1997 | Miura et al. | 562/519 |
| 5,756,836 | A | * | 5/1998 | Shimizu et al. | 562/519 |
| 5,916,422 | A | * | 6/1999 | Kimura et al. | 203/16 |
| 6,143,930 | A | * | 11/2000 | Singh et al. | 562/608 |
| 6,339,171 | B1 | * | 1/2002 | Singh et al. | 562/519 |
| 7,115,772 | B2 | * | 10/2006 | Picard et al. | 560/248 |
| 2006/0011462 | A1 | * | 1/2006 | Horiguchi et al. | 203/29 |
| 2006/0247466 | A1 | * | 11/2006 | Zinobile et al. | 562/517 |

FOREIGN PATENT DOCUMENTS
GB 893730 * 4/1962

* cited by examiner

*Primary Examiner* — Virginia Manoharan

(57) ABSTRACT

A method for removing acetaldehyde from a mixture of methyl acetate, methanol and acetaldehyde includes: (a) feeding the mixture of methyl acetate, methanol and acetaldehyde to a distillation column; (b) distilling the feed mixture of methyl acetate methanol and acetaldehyde at a pressure of 10 psig or more to generate an overhead vapor stream enriched in acetaldehyde as compared with the feed mixture and a residue stream depleted in acetaldehyde as compared with the feed mixture; and (c) withdrawing the residue stream depleted in acetaldehyde from the distillation column.

22 Claims, 8 Drawing Sheets

ACETALDEHYDE REMOVAL FROM METHYL ACETATE BY DISTILLATION AT ELEVATED PRESSURE

TECHNICAL FIELD

The present invention relates to aldehyde removal from a ternary mixture of methyl acetate, methanol and acetaldehyde. The purified methyl acetate/methanol mixture is particularly useful as a feedstock in a carbonylation process to produce acetic acid.

BACKGROUND OF THE INVENTION

Mixtures of methyl acetate and methanol are generated when producing polyvinyl alcohol by way of saponification of polyvinyl acetate. U.S. Pat. No. 7,115,772 to Picard et al. discloses a process wherein a methyl acetate/methanol mixture is recovered from a mother liquor of a saponification process. The '772 patent further suggests that the mixture can be used as a feedstock in a carbonylation process to make acetic acid. It was determined, however, that methyl acetate/methanol mixtures so produced contain significant levels of acetaldehyde which are believed to have a deleterious effect on impurities generated during carbonylation. In particular, it is believed that acetaldehyde present in a carbonylation reaction mixture produces propionic acid which is difficult and expensive to remove from acetic acid in order to meet product specifications.

Acetaldehyde is particularly difficult to remove from methyl acetate/methanol mixtures in spite of its relatively low boiling point (20.9° C.). So also, methanol is difficult to separate from methyl acetate because methanol and methyl acetate form a low boiling azeotrope. Thus, in conventional operations, methyl acetate is typically hydrolyzed to acetic acid and methanol prior to further purification and/or re-use as a feedstock.

It has been unexpectedly found in accordance with the present invention that acetaldehyde removal from a methyl acetate/methanol/acetaldehyde mixture by distillation is remarkably enhanced by conducting the distillation at elevated pressure and temperature. Thus purified, the methyl acetate/methanol mixture can be directly fed to a carbonylation unit to make acetic acid without the need for more elaborate treatment.

SUMMARY OF THE INVENTION

The present invention is directed at using a pressurized distillation column that is operated at higher temperatures than an atmospheric tower to remove AcH, as an overhead, from a MeOH/MeAc mixture. There is provided generally in accordance with the invention a process for the removal of acetaldehyde from a feed stream mixture comprising methyl acetate, methanol and acetaldehyde, by introducing the feed mixture to a distillation column, distilling the feed at a pressure of greater than atmospheric pressure, removing a low boiling overhead vapor stream enriched in acetaldehyde, and withdrawing a high boiling residue comprising methyl acetate, methanol, and reduced levels of acetaldehyde. If so desired, the purified mixture can be directly fed to a methanol carbonylation unit without further purification.

Without intending to be bound by theory, it is believed that methanol reversibly forms a high boiling hemicaetal with acetaldehyde at relatively low temperatures and that at the higher temperatures and pressures of the invention, the methyl acetate/methanol/acetaldehyde equilibrium favors the formation of low boiling "free" acetaldehyde which may be removed as a "light end" from the mixture. The equilibrium constant for the formation of the AcH/MeOH hemiacetal was confirmed to be temperature dependent. Higher temperatures were found to favor "free" AcH. The use of a single higher pressure distillation column that operated at higher distillation temperatures than an atmospheric tower was discovered to provide efficient AcH removal from MeAc even at high concentrations of MeOH, i.e., >20 wt %. In one example, a 60-tray distillation column was operated at 45 psig (overhead receiver pressure) with preheated MeAc/MeOH feed containing ~1200 ppm AcH. The feed tray was tray 40. The reflux-to-feed ratio was ~4.6:1.0. The overhead temperature at this operating pressure was ~93.9° C., which lowered the equilibrium concentration of the AcH/MeOH hemiacetal and, therefore, allowed for removal of "free" AcH as light-end impurity in the overhead distillate stream. Greater than 90% of the AcH in the feed was removed from the MeAc/MeOH mixture.

BRIEF DESCRIPTION OF THE DRAWINGS

The invention is described in detail below with reference to the following drawings.

DETAILED DESCRIPTION

The invention is described in detail below for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. %, ppm and like terms refer to wt. %, parts per million by weight and so forth, unless otherwise indicated.

"Distillation pressure" and like terminology refers to the pressure in the distillation tower, suitably measured at any level, but preferably measured in the overhead space of the tower.

"Distillation temperature" or like phrases refer to the temperature in the overhead stream of the distillation tower unless otherwise specified.

The following abbreviations are used herein for purposes of convenience:

AcH—acetaldehyde
DMA—dimethyl acetal

DME—dimethoxy ethane
EtAc—ethyl acetate
MeAc—methyl acetate
MeOH—methanol
OH—overhead
psig—gauge pressure
(R/F) ratio—reflux to feed ratio, W/W
res—residue Separation of AcH from MeAc appears possible by fractional distillation based on physical properties data (see Table 1, below); however, AcH is not readily separated from ternary mixtures of MeAc, MeOH and AcH as discussed below.

TABLE 1

Azeotropic Compositions and Boiling Points

| Components | B.P. °C. | Azeotrope B.P., °C. | wt % |
|---|---|---|---|
| AcH | 20.9 | — | — |
| MeOH | 64.7 | 54 | 18.7 |
| MeAc | 57 | | 81.3 |
| H2O | 100 | 70.4 | 8.1 |
| EtAc | 77.2 | | 91.9 |
| H2O | 100 | 61.3 | 3.6 |
| DME | 64.5 | | 96.4 |
| MeOH | 64.7 | 57.5 | 24.2 |
| DME | 64.5 | | 75.8 |

CRC Handbook, 50$^{th}$ Ed.

Preliminary studies at atmospheric pressure confirmed it was very difficult to separate AcH from MeAc in the presence of methanol, despite the low boiling point of AcH. For example, at feed methanol concentrations of >7% essentially all of the AcH fed to a distillation tower operated at atmospheric pressure exited in the residue stream.

Not intending to be bound by theory, the cause of the difficulty observed with separation of AcH from MeAc as a "light-end" was found to be primarily due to the presence of MeOH in the system. As shown in Equation 1 (below), methanol acting as a nucleophile added to the carbonyl carbon of AcH reversibly forming the corresponding hemiacetal.

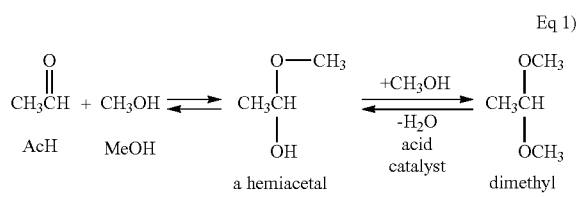

Eq 1)

Figure 1:
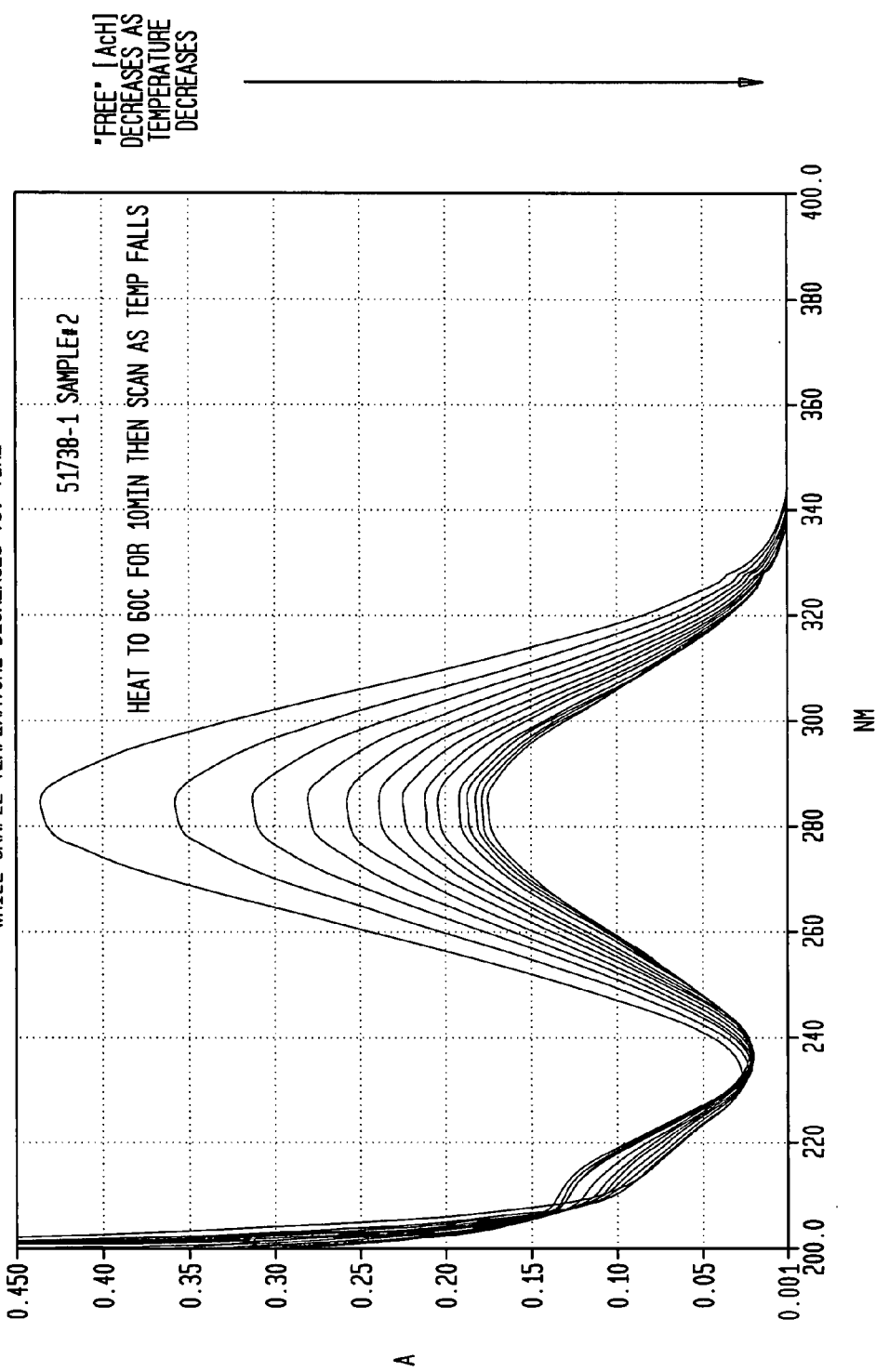
FIG. 1 is a plot of absorbance versus wavelength at decreasing temperatures showing the reduction in "free" AcH as temperature decreases.
Figure 2:
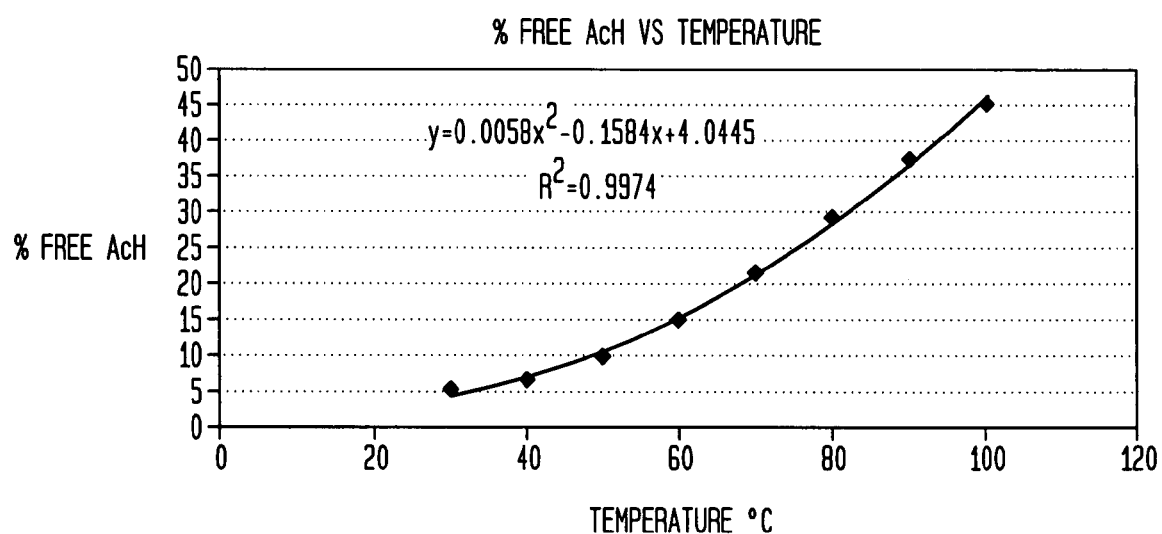
FIG. 2 is a plot % "free" AcH versus temperature.

The preliminary distillation experiments at atmospheric pressure were consistent with the hemiacetal having a lower volatility (higher boiling point) than AcH, which caused the hemiacetal to be concentrated in the distillation column residue stream. The estimated boiling point of methanol hemiacetal is about 109° C. at atmospheric pressure. Analyses of samples containing AcH and MeOH by gas chromatography were not able to detect the hemiacetal; however, UV/visible instrument experiments substantiated that the conversion of "free" AcH to the methanol hemiacetal was temperature dependent, as is seen in Example series A and B, as well as FIGS. 1 and 2.

EXAMPLE SERIES A

Preliminary Hemiacetal Studies

An ultra-violet spectrometer was calibrated with solutions of acetonitrile and methanol at varying concentrations (0.5%-1.0%). After calibration, a solution of approximately 1 wt % AcH in methanol was transferred to a vial, sealed and placed in a GC oven at 60° C. for 15 minutes. After 15 minutes the vial was quickly taken out and used to fill a spectrometer cell. After a thermocouple was placed inside the cell as well, the spectrometer was closed and scans and temperature readings were taken. Results appear in FIG. 1, wherein it is seen that the absorbance of "free" AcH at 285 nM decreased with temperature as the sample cooled.

Further studies (Example series B) were conducted using a modified high pressure liquid chromatography apparatus equipped with a UV/visible photodiode array detector.

EXAMPLE SERIES B

Secondary Hemiacetal Studies

The UV/visible photodiode array detector of a conventional HPLC (high pressure liquid chromatography) apparatus was calibrated using AcH standards prepared in HPLC grade acetonitrile. The standard solutions contained AcH concentrations in a range of from 0.1 wt % to 1.5 wt % to determine a Beer's Law molar absorptivity coefficient for AcH. Methanol solutions containing AcH concentrations in a range of from 0.5 wt % to 1.5 wt % were injected into the HPLC detector and absorbance readings were taken over a range of temperatures (30° C. to 100° C.). Results appear in FIG. 2 and Table 2, as well as FIG. 3.

TABLE 2

Temperature Dependence of Free Aldehyde Concentration

| Temperature °C. | Absorbance | free AcH (wt %) | % free AcH |
|---|---|---|---|
| 30 | 223 | 0.090 | 6.01 |
| 40 | 264 | 0.106 | 7.11 |
| 50 | 377 | 0.152 | 10.2 |
| 60 | 559 | 0.225 | 15.0 |
| 70 | 783 | 0.316 | 21.1 |
| 80 | 1053 | 0.425 | 28.4 |
| 90 | 1333 | 0.538 | 35.9 |
| 100 | 1600 | 0.645 | 43.1 |

Equilibrium constants were calculated from the experimental data and Arrhenius plots of Ln Keq versus 1/T ° K indicated a fairly good data fit and consistency between different data sets and literature values. The best-fit Keq relationship with respect to temperature for the reaction of AcH in MeOH to form the corresponding hemiacetal was developed using averaged data from the HPLC experiments along with two literature data points (see Eq 2, below).

$$Keq = 4.61 \times 10^{-7} \exp^{(8522/RT)}$$ Eq. 2)

where R=1.9872, and T=° K

The Keq equation (Eq. 2) was used to calculate equilibrium compositions at various temperatures and initial MeOH concentrations using an initial AcH concentration of 0.12 wt %. For example, a plot of temperature versus calculated % "free" AcH expected at equilibrium starting from initial MeOH concentrations ranging from 1000 ppm to 5 wt % was included in FIG. 3.

Figure 3:
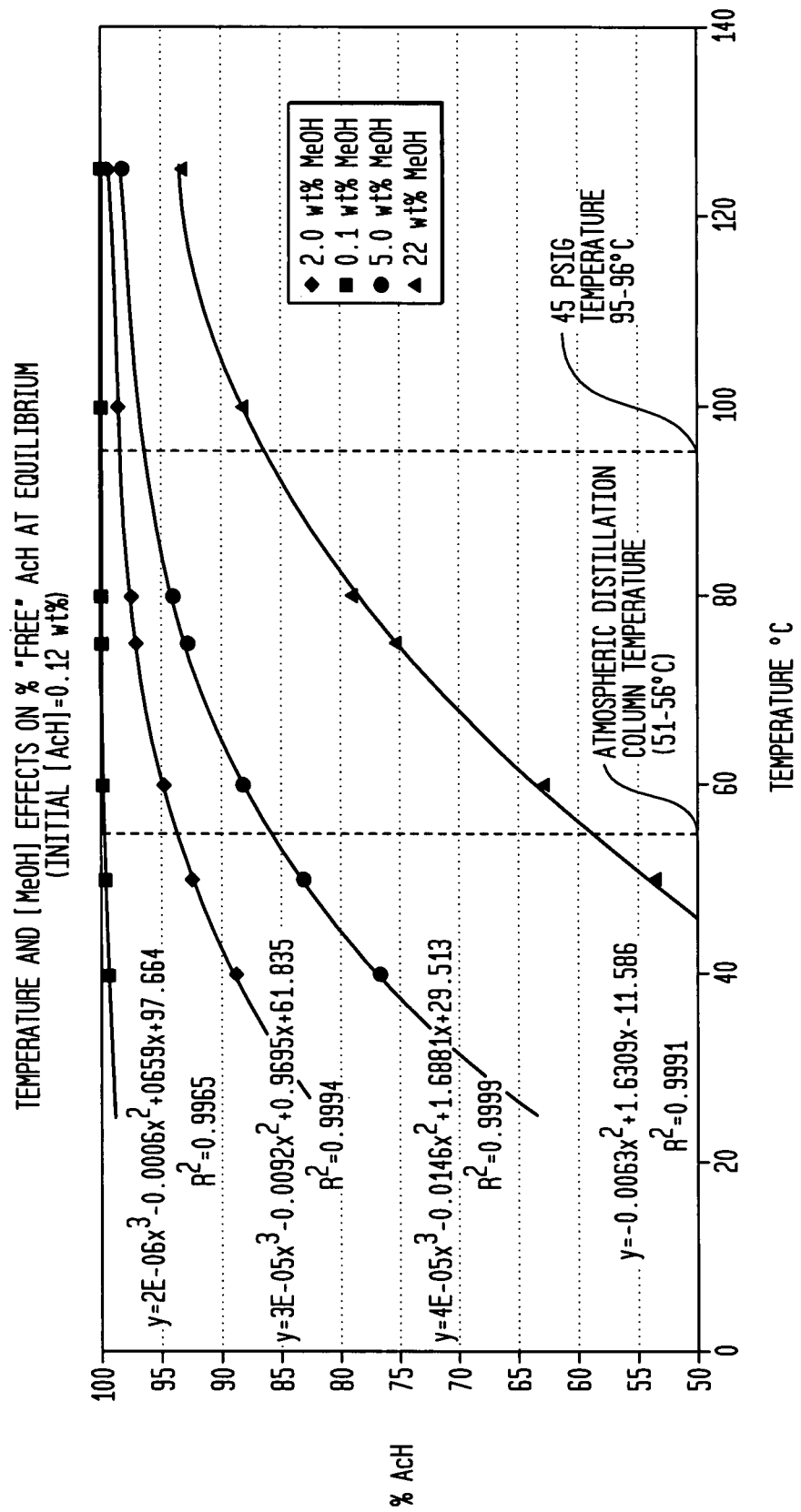
FIG. 3 is a plot of % "free" AcH versus temperature for different levels of MeOH in a ternary mixture of MeAc, MeOH and AcH.

It is appreciated from FIG. 3 that while the amount of free acetaldehyde decreases as the amount of methanol in the mixture increases, this trend may be reversed to favor free acetaldehyde by increasing the temperature and pressure.

Examples 1-16

Figure 4:
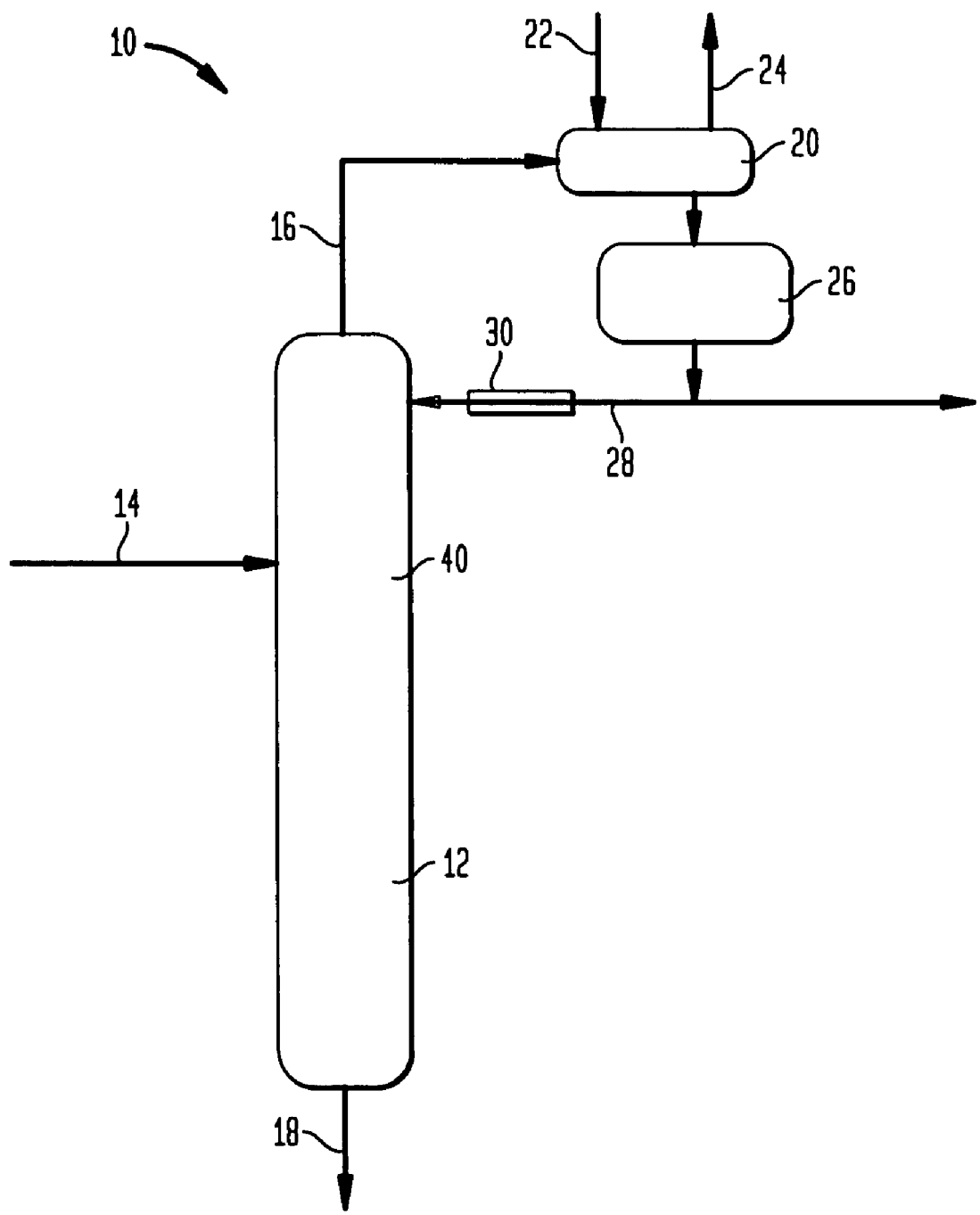
FIG. 4 is a schematic diagram illustrating an embodiment of the present invention utilizing a distillation system for the pressurized distillation of acetaldehyde from methyl acetate.

Referring to FIG. 4, a sixty (60) tray Oldershaw distillation apparatus 10 was used to distill ternary mixtures of MeAc, MeOH and AcH under pressure at elevated temperatures. Apparatus 10 includes a column 12 with sixty (60) trays provided with a feed inlet 14 at tray 40, an overhead outlet line at 16 and a residue outlet at 18. The overhead line is provided with a condenser 20 having an inlet 22 and an outlet 24 for coolant. Condenser 20 is coupled to a receiver 26 for receiving condensed overhead and providing it to a reflux line 28, which is optionally provided with a pre-heater 30.

Apparatus 10 was operated by feeding the ternary mixture MeAc, MeOH and AcH to inlet 14 of column 12, condensing column overhead in condenser 20 and feeding the condensed overhead as reflux through line 28 back to the column. Residue was withdrawn at 18, while condensed material was reboiled to maintain flux in the column.

A series of distillation runs were made at approximately 45 psig distillation operating pressures using MeAc spiked with AcH to achieve tower feedstock with a target AcH content of about 1200 ppm. The distillation runs were made with various reflux/feed (R/F), feed rates, and overhead condenser 20 coolant temperatures, as seen in Table 3. Condenser 20 temperatures, maintained by passing coolant through coolant inlet 22 and coolant outlet 24, affected the temperature of the overhead receiver 26 distillate, which was used for reflux, and the cooled reflux affected both internal reflux rates, and the equilibrium concentration of AcH and its corresponding MeOH hemiacetal in the reflux stream. Overhead condenser 20 cooler inlet 22 coolant temperature was increased (from a value of generally <10° C. for Examples 1-7) to new level of about 37° C. starting with Example 8. Also, reflux pre-heater 30 was added during the series of Examples starting with Example 14. The feed line was also pre-heated to control temperature.

Operating details and results for Examples 1-16 are summarized in Tables 3 and 4 and the discussion below.

Examples 1-7 were carried out with sub-cooled reflux at about 7° C.±4° C. at rates of 10.4±0.4 g/min, which corresponded to reflux-to-feed (R/F) ratio values in a range of from 2.63:1.0 to 6.45:1.0, see Table 3. The initial three Examples in this series (1, 2, and 3) had non-detectable levels of AcH in the residue product stream 18 samples; see Table 3. In Example 4, the apparatus was charged with 1246 ppm AcH in the MeAc/MeOH feedstock prior to start-up, and the overhead receiver 26 was charged with materials that had been further spiked with AcH to a concentration of 5.33 wt %. Example 5 was a continuation of Example 4. Both of these Examples (4 and 5) had low residue product stream AcH concentrations (i.e., 79 ppm and 1 ppm) even with the use of the spiked overhead (OH) receiver charge and subsequent reflux (OH samples) that contained 2.24 wt % and 1.69 w % AcH.

In Example 6, the apparatus was charged with about 5 wt % AcH in the overhead receiver 20 and Example 7 was started-up on an overhead receiver charge with about 10% AcH content. The residue stream AcH concentration was lowered to an acceptable level of about 76 ppm in Example 8, which was conducted with an initial overhead AcH concentration of 1 wt % that increased during the run. A reflux rate of 10.7 g/min (R/F=3.47:1.0) was typical, and the overhead condenser 30 coolant temperature was increased to about 37° C.

In Table 3 it is seen the R/F ratio was reduced to <2.32:1.0 for Examples 9-14 and the overhead coolant temperature was maintained at 38±2° C. Examples 9 and 10 were both started-up using reboiler and overhead receiver 26 material from the previous run, Example 8. As can be seen from the data in Table 4, the residue stream AcH concentrations were about 115 ±20 ppm for Examples 9 and 10 with corresponding overhead (OH) receiver (reflux) AcH concentrations in a range of about 3.3±0.3 wt %.

Examples 11, 12, 13, and 14 were conducted at a lower reflux to feed ratio of about 1.94±0.2:1.0 (see Table 3), and all of these distillation Examples resulted in unacceptably high residue AcH concentrations. Example 11 was started with an initial overhead receiver charge containing 5.6 wt % AcH and resulted in residue samples with 937-1434 ppm AcH. Example 12 residue contained about 737 ppm AcH and was started up on the reboiler and overhead mixtures from the proceeding Example 11. Example 13 was started up with reboiler and OH receiver material from the previous Example and residue samples showed AcH levels of up to 1568 ppm. Example 14 was conducted with a fresh overhead receiver MeAc/MeOH charge that was spiked to only approximately 2 wt % AcH, which resulted in residue stream AcH concentrations that were lowered only slightly to about 1050 ppm.

The overhead receiver 26 was charged with MeAc/MeOH spiked to contain 2 wt % AcH for Example 15, and the previous <2.32:1.0 R/F ratio was increased to a higher R/F ratio of 4.3:1.0. The residue stream contained about 0.16 wt % AcH for Example 15. The next run (Example 16) was started-up with a lower initial AcH concentration (i.e., 1 wt % AcH) in the overhead receiver 26, a reboiler charge of about 0.12 wt % AcH, and was operated at even a higher R/F ratio (i.e., 6.19:1.0). The residue AcH content was lowered to <500 ppm during this run.

Figure 5:
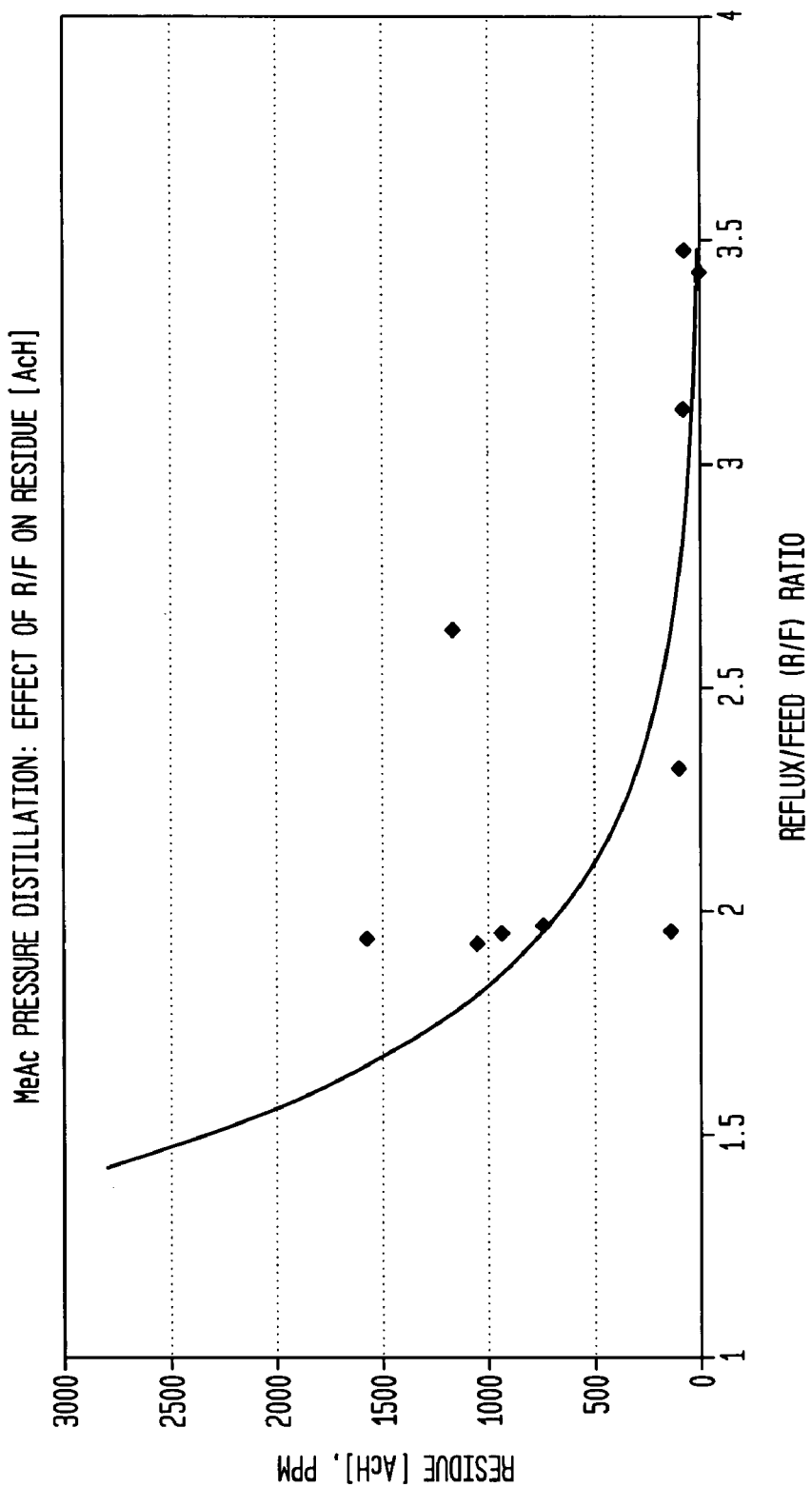
FIG. 5 is a plot of residue AcH concentration versus reflux to feed (R/F ratio)

FIG. 5 is a plot of product (residue) AcH in ppm versus R/F ratio wherein it is seen that removal efficiency increases dramatically at R/F rates greater than about 2. The residue AcH content (ppm) correlated with R/F ratio in accordance with the formula:

$$\text{Residue[AcH], ppm} = 102{,}000 \, e^{-2.53 \times R/F \, ratio} \qquad \text{Eq. 3}$$

TABLE 3

Operating Conditions and Calculations for Acetaldehyde Removal by Distillation at Elevated Pressure (45 psig)

| Example # | R/F Ratio | Reflux (g/min) | Feed (g/min) | Feed Preheat (° C.) | Coolant Temp (° C.) | OH [AcH] wt % | Residue [AcH] (ppm) | OH/Residue Ratio (w/w) | Feed AcH (ppm) | Feed AcH (g/hr) | OH ACH (g/hr) | Residue AcH (g/hr) |
|---|---|---|---|---|---|---|---|---|---|---|---|---|
| 1 | 6.25 | 10 | 1.6 | 72.3 | 3.5 | 0.848 | 0.5 | 16960 | 740 | 0.71 | 5.09 | 0 |
| 2 | 6.45 | 10 | 1.55 | 85.6 | 3.7 | 0.8029 | 0.5 | 16058 | 770 | 0.72 | 4.82 | 0 |
| 3 | 3.57 | 10.7 | 3 | | 11.2 | 0.3478 | 0.5 | 6956 | 770 | 1.39 | 2.23 | 0 |
| 4 | 3.13 | 10 | 3.2 | 84.6 | 5.69 | 2.24 | 79 | 283.54 | 1246 | 2.39 | 13.44 | 0.15 |
| 5 | 3.43 | 10.7 | 3.124 | 80.3 | 10.69 | 1.69 | 1 | 16900 | 1246 | 2.34 | 10.85 | 0 |
| 6 | 2.63 | 10.7 | 4.07 | 81.7 | 11 | 4.05 | 1172 | 34.56 | 1212 | 2.96 | 26 | 2.86 |

TABLE 3-continued

Operating Conditions and Calculations for Acetaldehyde Removal by Distillation at Elevated Pressure (45 psig)

| Example # | R/F Ratio | Reflux (g/min) | Feed (g/min) | Feed Preheat (° C.) | Coolant Temp (° C.) | OH [AcH] wt % | Residue [AcH] (ppm) | OH/Residue Ratio (w/w) | Feed AcH (ppm) | Feed AcH (g/hr) | OH ACH (g/hr) | Residue AcH (g/hr) |
|---|---|---|---|---|---|---|---|---|---|---|---|---|
| 7 | 3.45 | 10.7 | 3.099 | 82.3 | 10.5 | 5.2 | 2156 | 24.12 | 1212 | 2.25 | 33.38 | 4.01 |
| 8 | 3.47 | 10.7 | 3.08 | 79 | 36.7 | 2.37 | 76 | 311.84 | 1229 | 2.27 | 15.22 | 0.14 |
| 9 | 2.32 | 7.1 | 3.059 | 81.5 | 39 | 3.58 | 95 | 376.84 | 1228 | 2.25 | 15.25 | 0.17 |
| 10 | 1.96 | 6 | 3.064 | 80.2 | 38 | 2.97 | 133 | 233.31 | 1235 | 2.27 | 10.69 | 0.24 |
| 11 | 1.95 | 6 | 3.075 | 83.2 | 37.09 | 2.63 | 937 | 28.07 | 849 | 1.57 | 9.47 | 1.73 |
| 12 | 1.97 | 6 | 3.05 | 83.8 | 36.4 | 4.38 | 737 | 59.43 | 1198 | 2.19 | 15.77 | 1.35 |
| 13 | 1.94 | 6 | 3.1 | 83.5 | 36.9 | 4.64 | 1568 | 29.59 | 1198 | 2.23 | 16.7 | 2.92 |
| 14 | 1.93 | 6 | 3.115 | 78.7 | 39.78 | 2.28 | 1050 | 21.71 | 1340 | 2.5 | 8.21 | 1.96 |
| 15 | 4.3 | 12 | 2.792 | 81.3 | 39.5 | 2.09 | 1482 | 14.1 | 1340 | 2.24 | 15.05 | 2.48 |
| 16 | 6.19 | 12 | 1.938 | 71.9 | 39.7 | 1.05 | 366 | 28.69 | 1160 | 1.35 | 7.56 | 0.43 |

TABLE 4

Representative Analytical Results Summary for Acetaldehyde Removal by Distillation at Elevated Pressure (45 psig)

| | Sample | Component | AcH (ppm) | MeOH (%) | EtOH (ppm) | MeOAc (%) | DMA (ppm) | EtOAc (ppm) | Water (%) |
|---|---|---|---|---|---|---|---|---|---|
| Example 1 | A | Overhead | 4064 | 27.7 | nd | 71.8 | nd | 5 | 0.09 |
| | | Residue | 0 | 17 | nd | 82.66 | 38 | 423 | 0.29 |
| | B | Overhead | 8480 | 23.8 | nd | 75.27 | nd | 73 | 0.07 |
| | | Residue | 0 | 15.44 | nd | 84.34 | 34 | 334 | 0.18 |
| Example 2 | A | Overhead | 9957 | 25.76 | nd | 73.22 | 27 | 27 | 0.02 |
| | | Residue | 0 | 21.2 | nd | 78.63 | 24 | 294 | 0.14 |
| | B | Overhead | 8029 | 26.91 | nd | 72.25 | nd | 43 | 0.04 |
| | | Residue | 0 | 20.03 | nd | 79.8 | 26 | 273 | 0.14 |
| Example 3 | A | Overhead | 3478 | 27.46 | nd | 72.15 | nd | 103 | 0.03 |
| | | Residue | 0 | 15.37 | nd | 84.46 | 39 | 424 | 0.12 |
| Example 4 | A | Overhead | 7584 | 27.24 | nd | 71.93 | nd | 54 | 0.07 |
| | | Residue | 79 | 19.69 | nd | 80.18 | 28 | 283 | 0.11 |
| | B | Overhead | 22400 | 27.98 | nd | 69.47 | nd | 40 | 0.31 |
| | | Residue | 56 | 20 | nd | 79.87 | 25 | 270 | 0.09 |
| Example 5 | A | Overhead | 11600 | 28.34 | nd | 70.33 | 1560 | 81 | nd |
| | | Residue | 2 | 19.55 | nd | 80.32 | 28 | 350 | 0.09 |
| | B | Overhead | 16900 | 25.75 | nd | 72.36 | 1901 | 65 | nd |
| | | Residue | 1 | 20.64 | nd | 79.24 | 21 | 281 | 0.08 |
| Example 6 | A | Overhead | 23000 | 27.8 | nd | 69.82 | 693 | 59 | nd |
| | | Residue | 1513 | 20.27 | nd | 79.43 | 60 | 298 | 0.11 |
| | B | Overhead | 40500 | 27.55 | nd | 68.13 | 1038 | 75 | 0.16 |
| | | Residue | 1172 | 21.86 | nd | 77.88 | 56 | 199 | 0.12 |
| Example 7 | A | Overhead | 56300 | 26.62 | nd | 67.56 | 878 | 2 | 0.1 |
| | | Residue | 2007 | 22.64 | nd | 77.01 | 65 | 196 | 0.12 |
| | B | Overhead | 52000 | 26.5 | nd | 68.22 | 776 | nd | nd |
| | | Residue | 2156 | 20.75 | nd | 78.99 | 55 | 180 | 0.025 |
| Example 8 | A | Overhead | 16200 | 27.94 | nd | 70.37 | 232 | 2 | 0.045 |
| | | Residue | 98 | 21.02 | nd | 78.83 | 28 | 185 | 0.117 |
| | B | Overhead | 23700 | 31.9 | nd | 62.68 | 306 | 2 | 0.018 |
| | | Residue | 76 | 23.97 | nd | 75.89 | 25 | 167 | 0.116 |
| Example 9 | A | Overhead | 23100 | 27.9 | nd | 69.71 | 337 | 2 | 0.045 |
| | | Residue | 69 | 21.1 | nd | 78.79 | 26 | 175 | 0.08 |
| | B | Overhead | 35800 | 27.5 | nd | 68.82 | 488 | 2 | 0.05 |
| | | Residue | 95 | 21.4 | nd | 78.49 | 23 | 161 | 0.08 |
| Example 10 | A | Overhead | 22000 | 26.2 | nd | 71.48 | 299 | 2 | 0.09 |
| | | Residue | 118 | 21.1 | nd | 78.8 | 26 | 165 | 0.11 |
| | B | Overhead | 29700 | 26.7 | nd | 70.2 | 398 | 2 | 0.09 |
| | | Residue | 133 | 20.7 | nd | 79.16 | 24 | 167 | 0.11 |
| Example 11 | A | Overhead | 27300 | 27.5 | nd | 69.85 | 427 | nd | nd |
| | | Residue | 937 | 19.5 | nd | 80.28 | 48 | 226 | 0.1 |
| | B | Overhead | 27600 | 27.9 | nd | 69.09 | 447 | nd | 0.23 |
| | | Residue | 1434 | 21 | nd | 78.73 | 45 | 182 | 0.11 |
| Example 12 | A | Overhead | 30300 | 28 | nd | 68.75 | 358 | nd | 0.14 |
| | | Residue | 475 | 22.1 | nd | 77.68 | 39 | 99 | 0.19 |
| | B | Overhead | 43800 | 27.5 | nd | 67.93 | 463 | nd | 0.14 |
| | | Residue | 737 | 22.6 | nd | 77.14 | 36 | 92 | 0.17 |
| Example 13 | A | Overhead | 41300 | 27.2 | nd | 68.62 | 444 | nd | nd |
| | | Residue | 640 | 21.6 | nd | 78.14 | 42 | 100 | 0.18 |
| | B | Overhead | 46400 | 27.3 | nd | 68.01 | 471 | nd | nd |
| | | Residue | 1568 | 21.3 | nd | 78.36 | 43 | 99 | 0.17 |
| Example 14 | A | Overhead | 22900 | 29 | nd | 68.66 | 174 | nd | 0.03 |
| | | Residue | 1034 | 21.3 | nd | 78.41 | 44 | 110 | 0.17 |

TABLE 4-continued

Representative Analytical Results Summary for Acetaldehyde Removal by Distillation at Elevated Pressure (45 psig)

| | Sample | Component | AcH (ppm) | MeOH (%) | EtOH (ppm) | MeOAc (%) | DMA (ppm) | EtOAc (ppm) | Water (%) |
|---|---|---|---|---|---|---|---|---|---|
| | B | Overhead | 22800 | 28.87 | nd | 68.8 | 170 | nd | 0.03 |
| | | Residue | 1050 | 22.6 | nd | 77.12 | 39 | 99 | 0.16 |
| Example 15 | A | Overhead | 22400 | 28.97 | nd | 68.73 | 172 | nd | 0.04 |
| | | Residue | 1666 | 21.66 | nd | 77.98 | 46 | 107 | 0.18 |
| | B | Overhead | 20900 | 28.87 | nd | 68.02 | 142 | nd | nd |
| | | Residue | 1482 | 21.07 | nd | 78.58 | 43 | 103 | 0.18 |
| Example 16 | A | Overhead | 6952 | 11.27 | nd | 88.01 | 64 | nd | 0.016 |
| | | Residue | 216 | 29.37 | nd | 70.26 | 55 | 284 | 0.31 |
| | B | Overhead | 10500 | 29.4 | nd | 69.51 | 77 | nd | 0.026 |
| | | Residue | 366 | 21.37 | nd | 78.57 | 39 | 112 | nd | nd = non-detected

Example Series 17

Utilizing the procedure and apparatus noted above, a continuous distillation run, Example series 17, was conducted with operation over a period of four days. Feed composition and operating parameters are seen in Tables 5 and 6. The run was made at a pressure of about 45 psig during the first three and one half days and was lowered to about 30 psig for about the last 8.5 hours of the fourth day. Reflux-to-feed ratios were held at about 4.6:1.0 during the run. The data taken over the run showed that residue product AcH concentrations typically ran at about 100±50 ppm while operating at about 45 psig corresponding to overhead AcH levels of about 1.4±0.5 wt %. When the pressure was lowered to about 30 psig in day 4, the residue AcH concentrations increased to slightly over 250 ppm.

TABLE 5

Feed Composition Data for Continuous Acetaldehyde Removal by Distillation at 45 psig and Subsequently Lowered to 30 psig

| Component | Feed (wt %) |
|---|---|
| AcH | 0.1141 |
| MeOH | 22.1 |
| EtOH | 0 |
| MeOAc | 77.61 |
| DMA | 0.0023 |
| EtOAc | 0.013 |
| Water | 0.016 |

TABLE 6

Operating Conditions for Continuous Acetaldehyde Removal by Distillation at 45 psig and Subsequently Lowered to 30 psig

| Parameter | Day 1 | Day 2 | Day 3 | Day 4 |
|---|---|---|---|---|
| Feed (g/min) | 2.16 | 2.17 | 2.27 | 2.12 |
| Feed Line (° C.) | 81.07 | 82.23 | 79.91 | 71.75 |
| Feed Line Inlet (° C.) | 95.33 | 95.13 | 93.23 | 83.6 |
| Column Bottom (° C.) | 97.4 | 97.02 | 96.6 | 86.69 |
| Overhead Line (° C.) | 94.62 | 94.41 | 92.72 | 83.06 |
| Condenser Coolant Inlet Temperature (° C.) | 30 | 29.7 | 29.87 | 29.48 |
| Pressure (psig) | 45.8 | 45.8 | 46.5 | 30.4 |
| Distillate (g/min) | 0.0285 | 0.0326 | 0.0246 | 0.0969 |
| Reflux Line (° C.) | 30.82 | 30.08 | 29.77 | 30.35 |
| R/F Ratio | 4.64 | 4.62 | 4.4 | 4.72 |
| Reflux (g/min) | 10 | 10 | 10 | 10 |
| Residue (g/min) | 1.77 | 1.88 | 1.91 | 1.82 |
| % AcH Removal | 89.76 | 92.99 | 92.33 | 81.57 |

Figure 6:
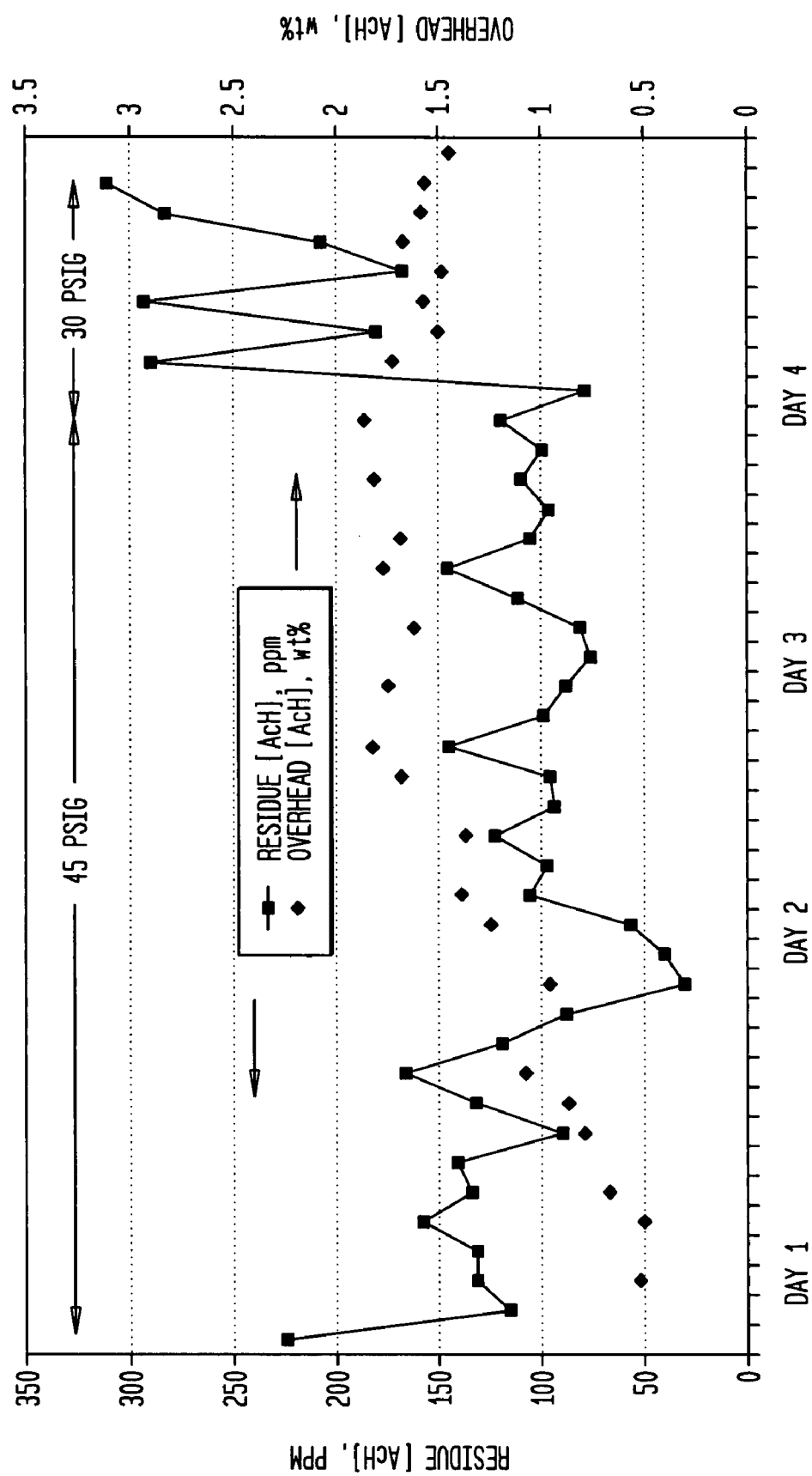
FIG. 6 is plot of AcH concentration data taken over a continuous distillation run (Example series 17) showing residue product AcH concentrations and overhead AcH concentrations throughout a four day run.

FIG. 6 is a plot of overhead and residue concentration of acetaldehyde during the continuous four day run, wherein it is seen the pressurized column efficiently removes acetaldehyde from the feed mixture. It is appreciated from FIG. 6 that as compared to essentially zero AcH removal from MeAc streams with high MeOH content when distilled at atmospheric pressure (0 psig), the % AcH removal was increased to ~82% and ~93% at operating pressures of ~30 psig and ~45 psig, respectively (using 1200 ppm AcH feedstock in a R/F ratio range of ~4.6:1.0). This result is indeed unexpected in view of the ineffectiveness of conventional low pressure distillation to remove acetaldehyde from mixtures of methyl acetate with methanol. The effects of elevated temperature and pressure as well as R/F ratio are further appreciated by reference to FIG. 7.

Figure 7:
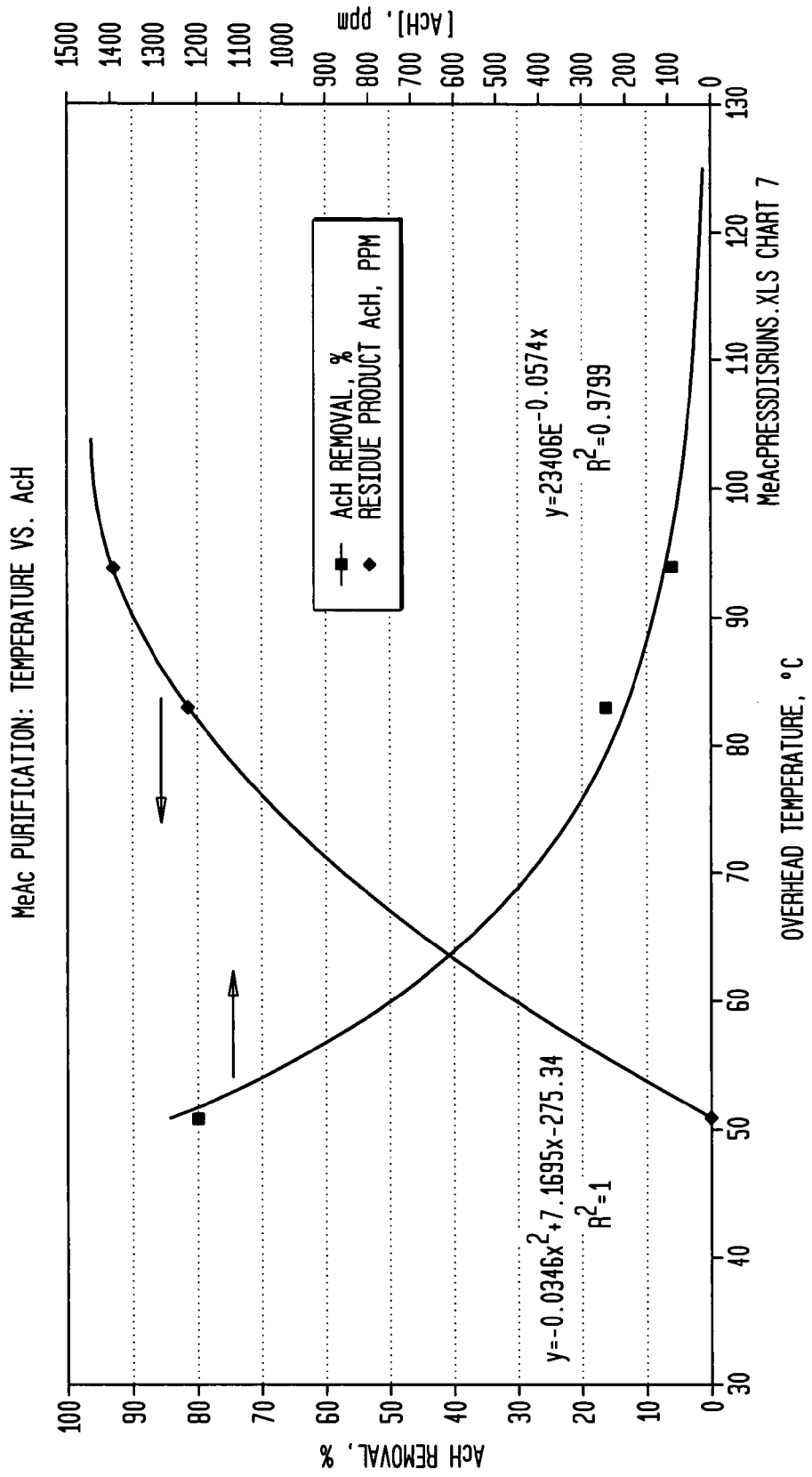
FIG. 7 is a plot of AcH removal and residue AcH concentration versus overhead temperature.

FIG. 7 is a plot of AcH removal (%) and product AcH content versus temperature, wherein it is seen that removal efficiency and product purity increase dramatically at overhead temperatures above about 70° C. or so.

The present invention thus provides a means for purifying a ternary mixture of methyl acetate, methanol and acetaldehyde by distillation at elevated pressures, preferably at least 10 psig. Operating pressures from 10 psig to 75 psig are suitable, such as from 20 psig to 50 psig or 25 to 50 psig. At these pressures, the temperature of the overhead is suitably maintained from about 70° C. to about 150° C. such as from about 85° C. to about 115° C. or about 90° C. to about 100° C. Reflux to feed ratios from 2 to 7 are suitable as are R/F ratio greater than 2, greater than 2.5, grater than 3 or greater than 4 within this R/F ratio range.

In various embodiments of the invention, the method is effective to purify the feed to AcH contents of less than 100 ppm or less than 50 ppm where the feed has an AcH content of more than 100 ppm, more than 250 ppm or 500 ppm; or more than 1000 ppm. The feed mixture may contain more than 1200 ppm acetaldehyde, such as 2000 ppm or up to 5000 ppm or up to 1 wt. % and optionally more AcH. The feed mixture may also contain from about 5% to 50% methanol such as from about 10% to 40% methanol or from about 15% to about 30% methanol in some cases.

Acetic Acid Production With Purified Methyl Acetate/Methanol Mixtures

Figure 8:
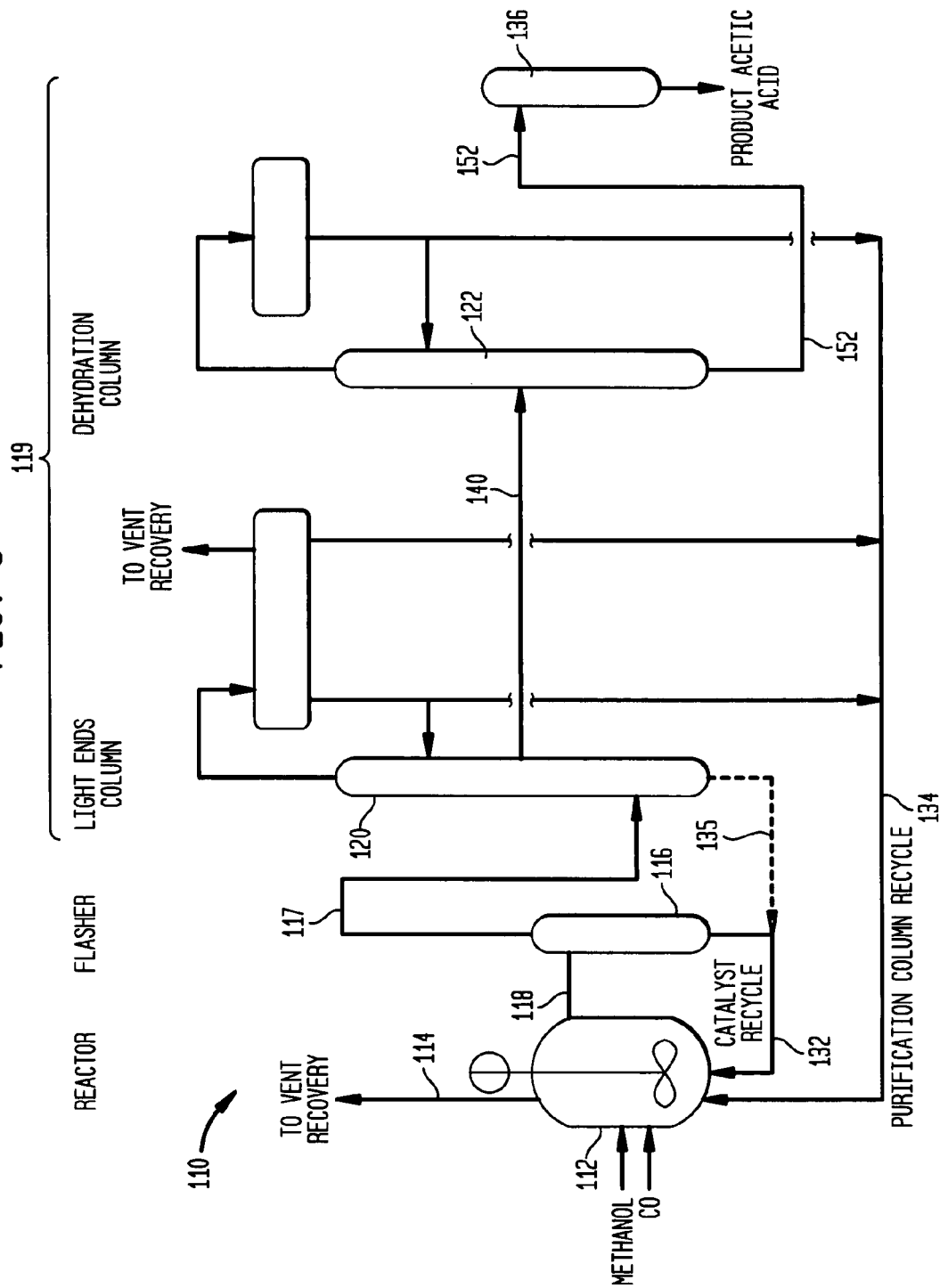
FIG. 8 is a schematic diagram illustrating a carbonylation system which may be used in connection with the present invention.

Methyl acetate/methanol mixtures purified in accordance with the invention may be fed directly to a methanol carbonylation unit as a feedstock to make acetic acid. A carbonylation unit 110 of this class is shown schematically in FIG. 8 along with associated purification. Carbon monoxide and a purified MeAc/MeOH stream of the invention (and optionally additional methanol or a reactive derivative thereof) are introduced continuously into reactor 112 with adequate mixing along with carbon monoxide at pressure. The non-condensable bi-products are vented from the reactor to maintain an optimum carbon monoxide partial pressure. In the reactor, a carbonylation reaction occurs to produce acetic acid while a suitable reaction mixture is maintained. The reaction mixture in reactor 112 includes a Group VIII metal catalyst, optionally an iodide salt, an alkyl halide promoter, carbon monoxide, acetic acid, methanol and/or reactive derivatives thereof, and water, as discussed in more detail hereinafter.

The Group VIII catalyst metal may be a rhodium and/or iridium catalyst. The rhodium metal catalyst may be added in any suitable form such that rhodium is in the catalyst solution as an equilibrium mixture including $[Rh(CO)_2I_2]^-$ anion as is well known in the art. When rhodium solution is in the carbon monoxide-rich environment of the reactor, solubility of the rhodium is generally maintained because rhodium/carbonyl iodide anionic species are generally soluble in water and acetic acid. However, when transferred to carbon monoxide depleted environments as typically exist in the flasher, light ends column and so forth, the equilibrium rhodium/catalyst composition changes since less carbon monoxide is available. Rhodium precipitates as $RhI_3$, for example; details as to the form of entrained rhodium downstream of the reactor is not well understood. Iodide salts help alleviate precipitation in the flasher under so-called "low water" conditions as will be appreciated by one of skill in the art.

Iodide salts maintained in the reaction mixtures may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide to generate the corresponding co-promoter iodide salt stabilizer. For additional detail regarding iodide salt generation; see U.S. Pat. No. 5,001,259 to Smith et al.; U.S. Pat. No. 5,026,908 to Smith et al.; and U.S. Pat. No. 5,144,068, also to Smith et al., the disclosures of which are hereby incorporated by reference.

Similarly, an iridium catalyst in the liquid carbonylation reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2)]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in the following U.S. Pat. Nos. 5,942,460; 5,932,764; 5,883,295; 5,877,348; 5,877,347 and 5,696,284, the disclosures of which are hereby incorporated by reference into this application as if set forth in their entirety.

An alkyl halide co-catalyst/promoter is generally used in combination with the Group VIII metal catalyst component. Methyl iodide is a preferred as the alkyl halide promoter. Preferably, the concentration of alkyl halide in the liquid reaction composition is in the range 1 to 50% by weight, preferably 2 to 30% by weight.

The alkyl halide promoter may be combined with a salt stabilizer/co-promoter compound, which may include salts of a metal of Group IA or Group IIA, or a quaternary ammonium or phosphonium salt. Particularly preferred are iodide or acetate salts, e.g., lithium iodide or lithium acetate.

Other promoters and co-promoters may be used as part of the catalytic system of the present invention as described in European Patent Publication EP 0 849 248, the disclosure of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of [0.5 to 15]:1, preferably [2 to 10]:1, more preferably [2 to 7.5]:1. A suitable promoter concentration is 400 to 5000 ppm.

The carbonylation reaction proceeds in reactor 112 as methanol and carbon monoxide reactants are continuously fed to the reactor. The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 Bar partial pressure, as its presence may result in the formation of hydrogenation products. The partial pressure of carbon monoxide in the reaction is suitably in the range 1 to 70 bar, preferably 1 to 35 bar, and most preferably 1 to 15 bar.

The pressure of the carbonylation reaction is suitably in the range 10 to 200 Bar, preferably 10 to 100 bar, most preferably 15 to 50 Bar. The temperature of the carbonylation reaction is suitably in the range 100 to 300° C., preferably in the range 150 to 220° C. Acetic acid is typically manufactured in a liquid phase reaction at a temperature of from about 150-200° C. and a total pressure of from about 20 to about 50 bar.

Acetic acid is typically included in the reaction mixture as the solvent for the reaction.

Suitable reactive derivatives of methanol include methyl acetate, dimethyl ether, methyl formate and methyl iodide. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range 0.5 to 70% by weight, preferably 0.5 to 50% by weight, more preferably 1 to 35% by weight and most preferably 1-20% by weight.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water maintained in the liquid reaction composition in reactor 112 is in the range 0.1 to 16% by weight, more preferably 1 to 14% by weight, most preferably 1 to 10% by weight, suitably less than 10 wt. % water.

From reactor 112, a stream of the reaction mixture is continuously fed via conduit 118 to flasher 116. Through the flasher the product acetic acid and the majority of the light ends (methyl iodide, methyl acetate, and water) are separated from the reactor catalyst solution, and the crude process stream 117 is forwarded with dissolved gases to the distillation or purification section 119 in single stage flash. The catalyst solution is recycled to the reactor via conduit 132. Under the process conditions of the flash, rhodium is susceptible to deactivation at the low carbon monoxide partial pressures in the flash vessel, and may be entrained to purification system 119.

The purification of the acetic acid typically includes distillation in a light ends column, a dehydration column, and, optionally, a heavy ends column. The crude vapor process stream 117 from the flasher is fed into the light ends column 120. Methyl iodide, methyl acetate, and a portion of the water condense overhead in the light end columns to form two phases (organic and aqueous). Both overhead phases return to the reaction section via recycle line 134. The dissolved gases from the light ends column vent through the distillation section. Before this vent stream is flared, residual light ends are scrubbed and recycled to the process. Optionally, a liquid recycle stream 135 from the light ends column may also be returned to the reactor.

The purified process stream 140 is drawn off the side of the light end column 120 and is fed to dehydration column 122. Water and some acetic acid from this column separate and are recycled to the reaction system via recycle line 134 as shown. The purified and dried process stream 152 from the dehydration column 122 feeds resin bed 136 and product is taken therefrom as shown. Carbonylation system 110 uses only 2 purification columns and is preferably operated as described in more detail in U.S. Pat. No. 6,657,078 to Scates et al., entitled "Low Energy Carbonylation Process", the disclosure of which is incorporated herein by reference.

"In an embodiment:
- A. A method for removing acetaldehyde from a mixture of methyl acetate, methanol and acetaldehyde comprising:
  - (a) feeding the mixture of methyl acetate, methanol and acetaldehyde to a distillation column;
  - (b) distilling the feed mixture of methyl acetate methanol and acetaldehyde at a pressure of 10 psig or more to generate an overhead vapor stream enriched in acetaldehyde as compared with the feed mixture and a residue stream depleted in acetaldehyde as compared with the feed mixture; and
  - (c) withdrawing the residue stream depleted in acetaldehyde from the distillation column.
- B. The method according to embodiment A, wherein the distillation column is operated at a pressure of from 10 psig to 75 psig.
- C. The method according to embodiment A, wherein the distillation column is operated at a pressure of from 20 psig to 55 psig.
- D. The method according to embodiment A, wherein the distillation column is operated at a pressure of from 25 psig to 50 psig.
- E. The method according to embodiment A, wherein the temperature of the overhead vapor stream is from about 70° C. to about 150° C.
- F. The method according to embodiment A, wherein the temperature of the overhead vapor stream is from about 85° C. to about 115° C.
- G. The method according to embodiment A, wherein the temperature of the overhead vapor stream is from about 90° C. to about 100° C.
- H. The method according to embodiment A, further comprising refluxing at least a portion of the overhead stream to the distillation column.
- I. The method according to embodiment H, wherein the distillation column is operated at a reflux to feed (R/F) ratio of greater than 2.
- J. The method according to embodiment H, wherein the distillation column is operated at a reflux to feed (R/F) ratio of greater than 2.5.
- K. The method according to embodiment H, wherein the distillation column is operated at a reflux to feed (R/F) ratio of greater than 3.
- L. The method according to embodiment H, wherein the distillation column is operated at a reflux to feed (R/F) ratio of greater than 4.
- M. The method according to embodiment H, wherein the distillation column is operated at a reflux to feed (R/F) ratio of from about 2 up to about 7.
- N. A method for removing acetaldehyde from a mixture of methyl acetate, methanol and acetaldehyde comprising:
  - (a) feeding a mixture of methyl acetate, methanol and acetaldehyde to a distillation column, wherein the feed mixture comprises at least about 5 wt.% methanol, more than 100 ppm acetaldehyde and the balance methyl acetate;
  - (b) distilling the feed mixture of methyl acetate, methanol and acetaldehyde at a pressure of 10 psig or more to generate an overhead vapor stream enriched in acetaldehyde as compared with the feed mixture and a residue stream depleted in acetaldehyde as compared with the feed mixture;
  - (c) refluxing a portion of the overhead stream to the distillation column;
  - (d) controlling the temperature of the overhead vapor stream, the pressure of the distillation column and the reflux to feed (R/F) ratio of the distillation column such that the residue stream has an acetaldehyde content of less than 100 ppm; and
  - (e) withdrawing the residue stream from the distillation column.
- O. The method according to embodiment N, wherein the feed mixture includes more than 250 ppm acetaldehyde.
- P. The method according to embodiment N, wherein the feed mixture includes more than 500 ppm acetaldehyde.
- Q. The method according to embodiment N, wherein the feed mixture includes more than 1000 ppm acetaldehyde.
- R. The method according to embodiment N, wherein the residue stream has less than 50ppm acetaldehyde.
- S. The method according to embodiment N, wherein the residue stream has less than 25ppm acetaldehyde.
- T. The method according to embodiment N, wherein the feed mixture includes from about 5 wt.% to about 50 wt.% methanol.
- U. The method according to embodiment N, wherein the feed mixture includes from about 10 wt.% to about 40 wt.% methanol.

V. The method according to embodiment N, wherein the feed mixture includes from about 15 wt.% to about 30 wt.% methanol.

W. The method according to embodiment N, wherein the feed mixture is derived from the production of polyvinyl alcohol from polyvinyl acetate by way of saponification.

X. A process for the production of acetic acid comprising:
(a) purifying a mixture of methyl acetate, methanol and acetaldehyde to remove acetaldehyde by way of (i) feeding the mixture of methyl acetate, methanol and acetaldehyde to a distillation column; (ii) distilling the feed mixture of methyl acetate methanol and acetaldehyde at a pressure of 10 psig or more to generate an overhead vapor stream enriched in acetaldehyde as compared with the feed mixture and a residue stream depleted in acetaldehyde as compared with the feed mixture; and (iii) withdrawing the residue stream depleted in acetaldehyde from the distillation column;
(b) feeding the purified residue stream to a carbonylation reaction mixture along with carbon monoxide, the carbonylation mixture comprising water, a catalyst selected from rhodium catalysts, iridium catalysts and mixtures thereof, a methyl iodide promoter and acetic acid; and
(c) recovering acetic acid from the carbonylation mixture.

Y. The method according to embodiment X, wherein the catalyst is a rhodium catalyst and the carbonylation reaction mixture contains less than 10% by weight water."

While the invention has been described with reference to the preferred embodiments, obvious modifications and alterations are possible by those skilled in the related art having the benefits of this disclosure. Therefore, it is intended that the invention include all such modifications and alterations to the full extent that they come within the scope of the following claims or the equivalents thereof.

What is claimed is:

1. A method for removing acetaldehyde from a mixture of methyl acetate, methanol and acetaldehyde comprising:
   (a) feeding the mixture of methyl acetate, methanol and acetaldehyde to a distillation column;
   (b) distilling the feed mixture of methyl acetate methanol and acetaldehyde at a pressure of 10 psig or more to generate an overhead vapor stream enriched in acetaldehyde as compared with the feed mixture and a residue stream depleted in acetaldehyde as compared with the feed mixture; and
   (c) withdrawing the residue stream depleted in acetaldehyde from the distillation column, wherein at least a portion of the overhead stream is refluxed to the distillation column wherein the distillation column is operated at a reflux to feed (R/F) ratio of greater than 2.

2. The method according to claim 1, wherein the distillation column is operated at a pressure of from 10 psig to 75 psig.

3. The method according to claim 1, wherein the distillation column is operated at a pressure of from 20 psig to 55 psig.

4. The method according to claim 1, wherein the distillation column is operated at a pressure of from 25 psig to 50 psig.

5. The method according to claim 1, wherein the temperature of the overhead vapor stream is from about 70° C. to about 150° C.

6. The method according to claim 1, wherein the temperature of the overhead vapor stream is from about 85° C. to about 115° C.

7. The method according to claim 1, wherein the temperature of the overhead vapor stream is from about 90° C. to about 100° C.

8. The method according to claim 1, wherein the distillation column is operated at a reflux to feed (R/F) ratio of greater than 2.5.

9. The method according to 1, wherein the distillation column is operated at a reflux to feed (R/F) ratio of greater than 3.

10. The method according to claim 1, wherein the distillation column is operated at a reflux to feed (R/F) ratio of greater than 4.

11. A method for removing acetaldehyde from a mixture of methyl acetate, methanol and acetaldehyde comprising:
    (a) feeding a mixture of methyl acetate, methanol and acetaldehyde to a distillation column, wherein the feed mixture comprises at least about 5 wt. % methanol, more than 100 ppm acetaldehyde and the balance methyl acetate;
    (b) distilling the feed mixture of methyl acetate, methanol and acetaldehyde at a pressure of 10 psig or more to generate an overhead vapor stream enriched in acetaldehyde as compared with the feed mixture and a residue stream depleted in acetaldehyde as compared with the feed mixture;
    (c) refluxing a portion of the overhead stream to the distillation column;
    (d) controlling the temperature of the overhead vapor stream, the pressure of the distillation column and the reflux to feed (RIF) ratio of the distillation column such that the residue stream has an acetaldehyde content of less than 100 ppm; and
    (e) withdrawing the residue stream from the distillation column.

12. The method according to claim 11, wherein the feed mixture includes more than 250 ppm acetaldehyde.

13. The method according to claim 11, wherein the feed mixture includes more than 500 ppm acetaldehyde.

14. The method according to claim 11, wherein the feed mixture includes more than 1000 ppm acetaldehyde.

15. The method according to claim 11, wherein the residue stream has less than 50 ppm acetaldehyde.

16. The method according to claim 11, wherein the residue stream has less than 25 ppm acetaldehyde.

17. The method according to claim 11, wherein the feed mixture includes from about 5 wt. % to about 50 wt. % methanol.

18. The method according to claim 11, wherein the feed mixture includes from about 10 wt. % to about 40 wt. % methanol.

19. The method according to claim 11, wherein the feed mixture includes from about 15 wt. % to about 30 wt. % methanol.

20. The method according to claim 11, wherein the feed mixture is derived from the production of polyvinyl alcohol from polyvinyl acetate by way of saponification.

21. A process for the production of acetic acid comprising:
    (a) purifying a mixture of methyl acetate, methanol and acetaldehyde to remove acetaldehyde by way of:
    (i) feeding the mixture of methyl acetate, methanol and acetaldehyde to a distillation column;
    (ii) distilling the feed mixture-of methyl acetate methanol and acetaldehyde at a pressure of 10 psig or more to generate an overhead vapor stream enriched in acetaldehyde as compared with the feed mixture and a residue stream depleted in acetaldehyde as compared with the feed mixture, wherein at least a portion of the overhead stream is refluxed to the distillation column, and wherein the distillation column is operated at a reflux to feed (R/F) ratio of greater than 2; and (iii) withdrawing the residue stream depleted in acetaldehyde from the distillation column;

(b) feeding the residue stream to a carbonylation reaction mixture along with carbon monoxide, the carbonylation mixture comprising water, a catalyst selected from rhodium catalysts, iridium catalysts or mixtures thereof, a methyl iodide promoter and acetic acid; and (c) recovering acetic acid from the carbonylation mixture.

22. The method according to claim 21, wherein the catalyst is a rhodium catalyst and the carbonylation reaction mixture contains less than 10% by weight water.

* * * * *